United States Patent [19]
Williams et al.

[11] Patent Number: 6,069,147
[45] Date of Patent: May 30, 2000

[54] THERMOGENESIS STIMULATING DRUGS

[75] Inventors: Gareth Williams; Chen Bing, both of Liverpool, United Kingdom; Elbert Kaan, Grossburgwedel; Dieter Ziegler, Hemmingen, both of Germany

[73] Assignee: Solvay Pharmaceuticals GmbH, Hannover, Germany

[21] Appl. No.: 09/286,301

[22] Filed: Apr. 6, 1999

[30] Foreign Application Priority Data

Apr. 6, 1998 [DE] Germany .............................. 198 15 411

[51] Int. Cl.$^7$ .................................................. A61K 31/506
[52] U.S. Cl. .............................................................. 514/269
[58] Field of Search ............................................... 514/269

[56] References Cited

PUBLICATIONS

Bing et al., Eur. J. Clin. Invest. (28, Suppl. 1, A32), 1998.

*Primary Examiner*—Pgyllis G. Spivack
*Attorney, Agent, or Firm*—Evenson, McKeown, Edwards & Lenahan, P.L.L.C.

[57] ABSTRACT

The use of moxonidine an its physiologically compatible acid-addition salts for the treatment and/or prophylaxis of disorders of thermogenesis and for the stimulation of thermogenesis in persons with abnormally reduced energy turnover and/or persons with reduced thermogenesis during or following a weight loss diet is disclosed.

7 Claims, No Drawings

THERMOGENESIS STIMULATING DRUGS

BACKGROUND OF THE INVENTION

The present invention relates to the use of 4-chloro-5-[(4,5-dihydro-1H-imidazol-2-yl)-amino]-6-methoxy-2-methylpyrimidine (moxonidine) and its physiologically acceptable acid-addition salts for the treatment and/or prophylaxis of disorders of thermogenesis and/or for the stimulation (increase) of thermogenesis in persons with abnormally low energy metabolism ("combustion") and/or in persons in whom thermogenesis is reduced during or following a weight-reducing diet, and to the manufacture of medicinal products suitable for this treatment and/or stimulation.

SUMMARY OF THE INVENTION

It is the object of the invention to provide new method of treating energy metabolism disorders due to insufficient thermogenesis.

A further object of the invention is to provide a new method of promoting thermogenesis, especially without cardiovascular stimulant side effects.

According to the invention, 4-chloro-5-[(4,5-dihydro-1H-imidazol-2-yl)-amino]-6-methoxy-2-methylpyrimidine of

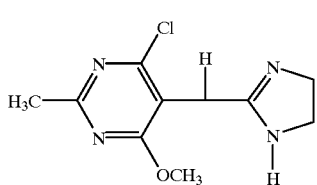

I and its physiologically compatible acid-addition salts are used in pharmaceutical preparations for enhancing thermogenesis and/or for the treatment and/or prophylaxis of thermogenic hypofunction, in particular without increasing blood pressure and heart rate.

The compounds used in accordance with the invention fall within the class of 5-[(2-imidazolin-2-yl)-amino]-pyrimidine derivatives with blood pressure lowering properties described in published German Patent Application No. DE 28 49 537, and are known from this patent application. Pharmaceutical preparations containing moxonidine are commercially available as anti-hypertensive medications under the trade name Physioten® and are used medically as antihypertensive agents. The compounds can be manufactured in a known manner in accordance with the processes described in the aforementioned published Patent Application or in a manner similar to these processes.

It has surprisingly been found that moxonidine and its physiologically compatible acid-addition salts have a thermogenesis promoting action in man and larger mammals and are suitable for the treatment of disorders of energy metabolism associated with insufficient thermogenesis.

The energy balance of a patient may be disordered such that he is suffering from a thermogenic hypofunction and his basic metabolic rate is by nature so low that the consumed amounts of food are not completely utilized thermogenically for conversion into combustion energy, but are partly converted into fat and stored in adipocytes, and such that the metabolic utilization of fat is inadequate due to the insufficient thermogenic activity.

Thermogenesis disorders can occur, for example, during and after weight-reducing diets, since the body responds to inadequate food consumption by a reflexive reduction in thermogenic activity, putting this activity as it were "on the back burner," and even when normal adequate food intake is resumed, thermogenesis remains at an undesired reduced level, and the fat deposits depleted during the diet are replenished.

Stimulation of thermogenesis is therefore required for preventing a reflexive inhibition of thermogenesis during and after a weight-reducing diet and/or medication (e. g. with appetite suppressants) and in order to avoid subsequent renewed weight gain.

Thermogenesis disorders which can lead to disturbances of thermoregulation with resulting hypothermia (i.e., a lowering of the body temperature to below normal values) and which lend themselves to treatment also may occur as a result of, for example, excessively long exposure to cold or excessively long immersion in cold water and/or as a secondary condition associated with various diseases.

Because of its thermogenesis promoting action, moxonidine is suitable for stimulating both the thermogenic activity of the tissues that produce combustion energy and the metabolism in the adipocytes, and for increasing the basic thermogenic turnover.

Metabolism stimulating drugs frequently also have a stimulating effect on cardiovascular functions and can thereby cause increases in blood pressure. Moxonidine used to stimulate thermogenesis in accordance with the invention is distinguished by a surprisingly different activity profile in which centrally acting thermogenesis promoting properties are associated with blood pressure lowering actions. Moxonidine induces stimulation of the tissue that produces the combustion energy while simultaneously depressing cardiovascular function. This favorable activity profile of the thermogenesis enhancing activity of moxonidine is due to its being induced mainly through the central effects of moxonidine on the thermogenesis regulatory centers in the hypothalamus.

Since obesity is often associated with elevated blood pressure and/or heart complaints, a drug that counteracts thermogenic hypofunction and increases thermogenic energy consumption without exhibiting blood pressure increasing side effects, and which even additionally possesses blood pressure lowering properties, is particularly beneficial.

DESCRIPTION OF PREFERRED EMBODIMENTS

In order to treat states of disturbed and/or undesirably reduced thermogenesis in accordance with the invention, moxonidine and its physiologically compatible acid-addition salts can be administered orally, intravenously or transdermally in conventional pharmaceutical preparations.

Suitable physiologically acceptable acid-addition salts of moxonidine include salts with inorganic acids, for example hydrogen halide acids such as hydrochloric acid, or with organic acids, for example lower aliphatic monocarboxylic or dicarboxylic acids such as acetic acid, fumaric acid or tartaric acid or aromatic carboxylic acids such as salicylic acid.

For example, according to the invention the active quantities of the compounds that stimulate thermogenesis can be contained together with customary pharmaceutical adjuvants (i.e., excipients and/or additives) in solid or liquid pharmaceutical formulations. Examples of solid dosage forms include suppositories or preparations suitable for oral administration such as tablets, coated tablets, capsules, powders or granules. These solid dosage forms can contain standard pharmaceutical inorganic and/or organic excipients such as lactose, talc or starch in addition to customary pharmaceutical additves such as lubricants or tablet disintegrating agents. Liquid preparations such as solutions, suspension or emulsions of the active ingredients can contain the usual diluents such as water, oil and/or suspending aids such as polyethylene glycols and the like. Further additives such as preservatives, flavoring agents and the like may also be added.

The active ingredients can be mixed and formulated with the pharmaceutical excipients and/or additives in an essentially known manner. For the manufacture of solid dosage forms, for example, the active ingredients may be mixed with the excipients and/or addtives in the usual manner and granulated in a wet or dry process. Granules or powder can be filled directly into capsules or compressed in the usual manner into tablet cores. If desired, the tablet cores can be coated in a known manner.

The thermogenesis promoting activity of moxonidine can be demonstrated in Zucker rats by standard tests for the detection of pharmacological indicators for the action of moxonidine on the factors influencing thermogenesis.

It has been shown that in obese Zucker rats the content of uncoupling protein-1 (UCP-1) mRNA was significantly reduced compared to that of lean animals of the same species. This reflects a disturbed thermogenic function which in this animal model is probably attributable to a central genetically controlled dysfunctional regulation of the sympathetic nervous system.

Test Description

Nine lean and 18 obese 9-week-old Zucker rats received moxonidine in a daily dose of 3 mg/kg orally for 21 days. The same number of control animals received only placebo. The animals had unlimited access to food.

The neuropeptide Y (=NPY) mRNA level in the hypothalamic tissue was determined. NPY is a neuropeptide which promotes obesity due to its appetite stimulating and anti-thermogenic properties. In the tissue of the obese rats treated with moxonidine the NPY mRNA levels were reduced by 40% compared to the control animals. In the lean animals, however, no significant reduction of NPY mRNA levels was observed. These data indicate that moxonidine has a central inhibiting effect on NPY synthesis in the arcuate nuclei (ARC), which contributes to activating the energy utilizing tissue and increasing the thermogenic activity in the fatty tissue, e. g. in Brown Adipose Tissue (BAT).

Furthermore, as an indication of the thermogenic activity in BAT, the UCP-1 mRNA levels in BAT were also determined by Northern Blotting analysis. Moxonidine approximately doubles the UCP-1 gene expression in adipose and lean animals compared to controls.

The experiments with obese animals were repeated under pair-fed conditions (i.e., the moxonidine treated animals were provided with unlimited amounts of food and the control animals received only an amount corresponding to the amount of food consumed by the moxonidine treated animals) in order to eliminate the influence of varying food intake between the control animal group and the moxonidine treated animal group on the investigated parameters.

In this experiment a three-fold increase of the UCP-1-gene expression was seen for the moxonidine treated animals as compared to the pair-fed control animal group.

These results are a clear indication that thermogenesis is increased after administration of moxonidine. The foregoing test results are an indicator that moxonidine has a central, thermogenesis promoting action. The foregoing experimental results show that moxonidine and its acid-addition salts exert a thermogenesis enhancing activity in cases of disturbed and undesirably reduced thermogenesis and thereby induce an increase in energy turnover without, however, impairing normal energy metabolism. Moxonidine and its acid-addition salts are therefore suitable for the treatment of thermogenic hypofunction and/or disturbed and/or undesirably reduced thermogenesis.

The doses to be administered may differ from individual to individual and naturally will vary depending on the type of condition to be treated and the form of administration. Generally, the daily doses for the treatment of states of disordered and/or undesirably reduced thermogenesis in man will lie in the range from 0.05 to 5 mg, preferably 0.2 to 0.8 mg, for oral administration.

The following example is intended as a more detailed illustration of the manufacture of a pharmaceutical preparation containing moxonidine that is suitable for the treatment of insufficient thermogenesis, without, however, limiting the scope of the invention.

EXAMPLE 1

Film-coated tablets containing moxonidine
Composition:

| Tablet cores: | |
|---|---|
| Moxonidine | 0.020 parts |
| Lactose | 9.580 parts |
| Povidone USP | 0.070 parts |
| Crospovidone USP | 0.300 parts |
| Magnesium stearate | 0.030 parts |
| (Water | 0.750 parts) |
| Total solids | 10.000 parts |
| Film coating: | |
| Hydroxypropyl methylcellulose | 0.156 parts |
| 30% aqueous ethylcellulose dispersion | 0.480 parts |
| (equivalent solids) | (0.144 parts) |
| Polyethylene glycol 6000 | 0.030 parts |
| Titanium dioxide | 0.150 parts |
| Talc | 0.1197 parts |
| Red iron oxide | 0.0003 parts |
| (Water | 3.864 parts) |
| Total solids | 0.600 parts |
| Total amount of film-coating suspension | 4.800 parts |

4.8 kg of the above film-coating suspension are used to coat 10,000 tablet cores weighing 100 mg each.

Manufacture of Tablet Cores

The moxonidine and lactose were mixed together. The mixture was thoroughly moistened with a solution of the binder povidone in water, thoroughly kneaded, and the resulting product was spread out on trays and dried at a temperature of about 50° C. to a residual moisture content of not more than 0.5%. The dried product was passed through a 0.75 mm sieve (Frewitt machine). After mixing the resulting granules with crospovidone and magnesium stearate, tablet cores weighing 100 mg each were compressed from this material such that each tablet core contained 20 mg of active ingredient.

Manufacture of the Film Coating Suspension

The hydroxypropyl methylcellulose and polyethylene glycol 6000 were dissolved in 1 part of the water. A suspension of talc, titanium dioxide and iron oxide in the remaining water was added to this solution with stirring. The resulting suspension was diluted with the 30% aqueous ethylcellulose dispersion with gentle stirring.

Film Coating of Tablet Cores

The film coating suspension was sprayed onto the tablet cores in a film coating apparatus, while warm air at about 70° C. heated the tablet cores to a temperature of about 45° C. The film-coated tablets were then dried for 16 hours at a temperature of about 45° C.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A method of enhancing thermogenesis or treating or inhibiting thermogenic hypofunction in a mammal, said method comprising the step of administering to said mammal an effective thermogenesis stimulating amount of 4-chloro-5-[(4,5-dihydro-1H-imidazol-2-yl)-amino]-6-methoxy-2-methylpyrimidine corresponding to the formula I

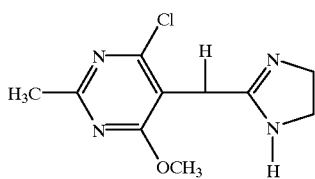

or a physiologically acceptable acid-addition salt thereof.

2. A method of enhancing thermogenesis or treating or inhibiting thermogenic hypofunction in a mammal, said method comprising the step of administering to said mammal a pharmaceutical composition comprising a thermogenically effective amount of 4-chloro-5-[(4,5-dihydro-1H-imidazol-2-yl) -amino]-6-methoxy-2-methylpyrimidine corresponding to the formula I

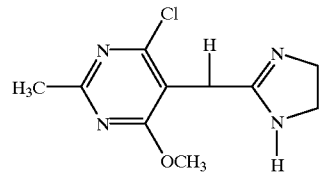

or a physiologically acceptable acid-addition salt thereof and at least one pharmaceutical carrier or adjuvant.

3. A method according to claim 2, wherein said pharmaceutical composition is administered orally in an amount sufficient to provide a daily dose in the range from 0.05 to 5 mg of said compound of formula I.

4. A method according to 3, wherein said pharmaceutical composition is administered in an amount sufficient to provide a daily dose in the range from 0.2 to 0.8 mg of said compound of formula I.

5. A method according to claim 2, wherein said pharmaceutical composition comprises a physiologically acceptable salt of said compound of formula I with an acid selected from the group consisting of hydrogen halide acids, lower aliphatic monocarboxylic or dicarboxylic acids, and aromatic carboxylic acids.

6. A method according to claim 2, wherein said acid is selected from the group consisting of hydrochloric acid, acetic acid, fumaric acid, tartaric acid, and salicylic acid.

7. A method according to claim 2, wherein said pharmaceutical composition comprises at least one adjuvant selected from the group consisting of lactose, talc, starch, lubricants, tablet disintegrating agents, water, oil, suspending aids, polyethylene glycols, preservatives and flavoring agents.

* * * * *